(12) United States Patent
Kuboi et al.

(10) Patent No.: US 10,178,945 B2
(45) Date of Patent: Jan. 15, 2019

(54) SHAPE SENSOR AND TUBULAR INSERTION SYSTEM

(71) Applicant: OLYMPUS CORPORATION, Tokyo (JP)

(72) Inventors: Toru Kuboi, Hachioji (JP); Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 495 days.

(21) Appl. No.: 14/960,811

(22) Filed: Dec. 7, 2015

(65) Prior Publication Data

US 2016/0081761 A1 Mar. 24, 2016

Related U.S. Application Data

(63) Continuation of application No. PCT/JP2014/064720, filed on Jun. 3, 2014.

(30) Foreign Application Priority Data

Jun. 7, 2013 (JP) .................................. 2013-121188

(51) Int. Cl.
*A61B 1/005* (2006.01)
*G01B 11/24* (2006.01)
(Continued)

(52) U.S. Cl.
CPC .......... *A61B 1/005* (2013.01); *A61B 1/00004* (2013.01); *A61B 1/0055* (2013.01);
(Continued)

(58) Field of Classification Search
CPC . A61B 1/00004; A61B 1/00055; A61B 1/005; A61B 1/0055; A61B 19/5244;
(Continued)

(56) References Cited

U.S. PATENT DOCUMENTS 7,440,661 B2 10/2008 Kobayashi
2006/0013523 A1* 1/2006 Childlers ........... A61B 1/00165
385/12
(Continued)

FOREIGN PATENT DOCUMENTS

EP 1 744 165 A1 1/2007
JP 04214042 A * 8/1992 ....... C03B 37/01214
(Continued)

OTHER PUBLICATIONS

International Search Report dated Jul. 15, 2014 issued in PCT/JP2014/064720.
(Continued)

*Primary Examiner* — Bo Joseph Peng
(74) *Attorney, Agent, or Firm* — Scully, Scott, Murphy & Presser, P.C.

(57) ABSTRACT

A shape sensor comprises a shape sensor main body which comprises an optical fiber capable, a detection object section, and a light detecting section to detect the detection light and which is capable of measuring a shape of a measurement target object by utilizing a change in characteristics of the light detected through the detection object section in accordance with a change in curvature of the optical fiber when the optical fiber curves; and a curving direction regulating section which is provided on at least a part of the optical fiber along an optical axis thereof and regulates a curvable direction of the optical fiber to a desired direction; wherein the curving direction regulating section is a core member which is disposed in at least a part of the shape sensor main body along the light propagating direction of the optical fiber and whose main curving direction is regulated.

11 Claims, 8 Drawing Sheets

(51) Int. Cl.
*G02B 23/24* (2006.01)
*A61B 1/00* (2006.01)
*A61B 19/00* (2006.01)
*A61B 34/20* (2016.01)

(52) U.S. Cl.
CPC ...... *A61B 1/00055* (2013.01); *A61B 19/5244* (2013.01); *G01B 11/24* (2013.01); *G02B 23/24* (2013.01); *A61B 2019/5261* (2013.01); *A61B 2034/2061* (2016.02)

(58) Field of Classification Search
CPC .... A61B 2019/5261; A61B 2034/2061; G01B 11/24; G02B 23/24
See application file for complete search history.

(56) References Cited

U.S. PATENT DOCUMENTS

| | | | |
|---|---|---|---|
| 2007/0116415 | A1 | 5/2007 | Kobayashi |
| 2008/0285909 | A1* | 11/2008 | Younge .............. A61B 5/1076 385/13 |
| 2009/0137952 | A1 | 5/2009 | Ramamurthy et al. |
| 2011/0202069 | A1 | 8/2011 | Prisco et al. |

FOREIGN PATENT DOCUMENTS

| | | | |
|---|---|---|---|
| JP | H04-261635 A | 9/1992 | |
| JP | H09-028664 A | 2/1997 | |
| JP | 10048487 A * | 2/1998 | .............. G02B 6/44 |
| JP | 2002-085335 A | 3/2002 | |
| JP | 2003-019109 A | 1/2003 | |
| JP | 2003-061902 A | 3/2003 | |
| JP | 2003-156367 A | 5/2003 | |
| JP | 2004-361285 A | 12/2004 | |
| JP | 2005-027725 A | 2/2005 | |
| JP | 2010-075322 A | 4/2010 | |
| JP | 4714570 B2 | 6/2011 | |

OTHER PUBLICATIONS

Extended Supplementary European Search Report dated Jan. 4, 2017 in related European Patent Application No. 14 80 8353.8.
Japanese Office Action dated Jun. 6, 2017 in Japanese Patent Application No. 2013-121188.
Chinese Office Action dated Jun. 2, 2017 in Chinese Patent Application No. 201480032410.2.
English translation of International Preliminary Report on Patentability dated Dec. 17, 2015 together with the Written Opinion received in related International Application No. PCT/JP2014/064720.
Chinese Office Action dated Apr. 23, 2018 in Chinese Patent Application No. 201480032410.2.

* cited by examiner

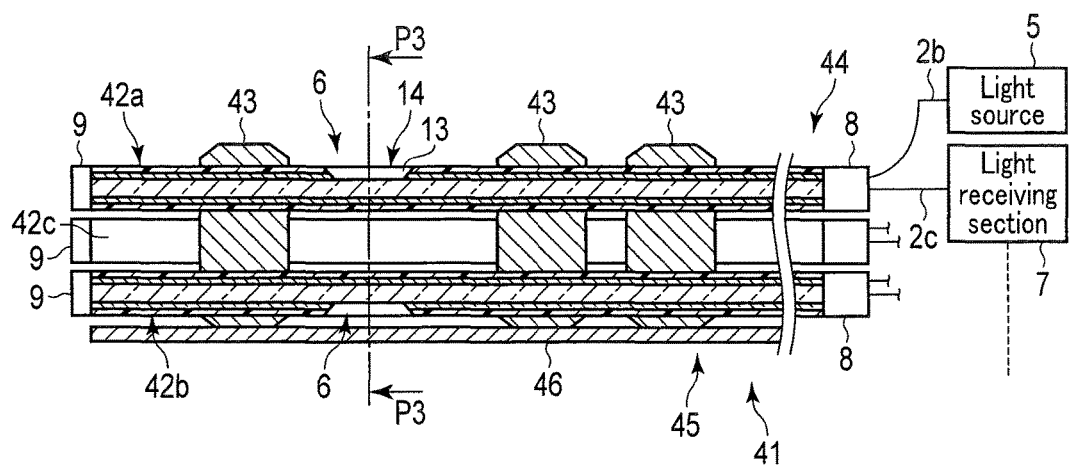
F I G. 6
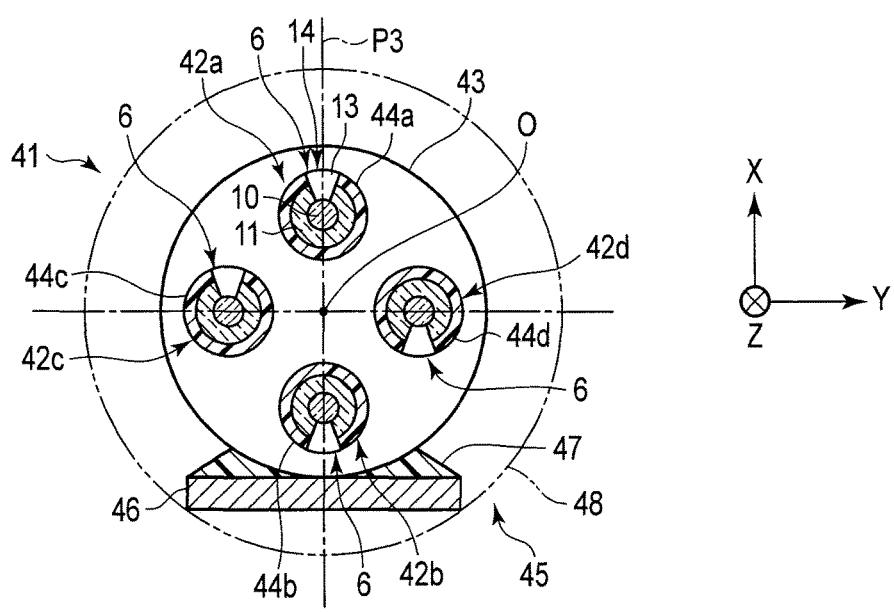
F I G. 7

SHAPE SENSOR AND TUBULAR INSERTION SYSTEM

CROSS-REFERENCE TO RELATED APPLICATIONS

This is a Continuation Application of PCT Application No. PCT/JP2014/064720, filed Jun. 3, 2014, which was published under PCT Article 21(2) in Japanese.

This application is based upon and claims the benefit of priority from prior the Japanese Patent Application No. 2013-121188, filed Jun. 7, 2013, the entire contents of which are incorporated herein by references.

BACKGROUND ART

1. Technical Field

The present invention relates to a shape sensor to detect a shape of a measurement target object, and a tubular insertion system having the shape sensor mounted therein.

2. Description of Related Art

An endoscope inserting section that has a curving section and is inserted into a body cavity bends along curves in the body cavity. For example, Japanese Patent No. 4714570 describes a shape detection probe (which will hereinafter be referred to as the shape sensor) that is assembled to the inserting section of the endoscope, bends integrally with the inserting section, and detects a bent shape. Herein, detection light emitted from a light source to detect a curvature is transmitted to a distal end side through a light supply fiber.

At an exit end of the light supply fiber, a mirror is provided, and reflected light of the detection light reflected by the mirror enters a curvature detection fiber, and this reflected light is received by a light receiving element. Further, in the vicinity of a surface of the curvature detection fiber, optical loss sections that absorb a part of the reflected light are provided. Amounts of the reflected light absorbed by the optical loss sections differ depending on curvatures of fiber bundles at positions where the optical loss sections are provided. Thus, in the patent literature, there is described a configuration to calculate the curvatures of the fiber bundles based on intensities of the reflected lights before and after passing through the optical loss sections.

SUMMARY OF INVENTION

According to an embodiment of the present invention, there is provided an shape sensor comprising: a shape sensor main body which comprises a light source, an optical fiber configured to propagate desired detection light emitted from the light source, a detection object section arranged in a part of the optical fiber, and a light detecting section to detect the detection light propagated through the optical fiber and which is configured to measure a shape of a measurement target object by utilizing a change in characteristics of the light detected through the detection object section in accordance with a change in curvature of the optical fiber when the optical fiber curves, and a curving direction regulating section which is provided on at least a part of the optical fiber along an optical axis thereof and regulates a curvable direction of the optical fiber to a desired direction, wherein the curving direction regulating section is a core member which is disposed in at least a part of the shape sensor main body along the light propagating direction of the optical fiber and whose main curving direction is regulated.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 6 is a longitudinal sectional view showing an outline configuration of an entire shape sensor according to a fourth embodiment of the present invention;

FIG. 7 is a cross-sectional view taken along a line P3-P3 depicted in FIG. 6;

DESCRIPTION OF EMBODIMENTS

A shape sensor and a tubular insertion system having this shape sensor mounted therein according to each embodiment of the present invention will now be described hereinafter with reference to the drawings.

[First Embodiment]

Figure 1:
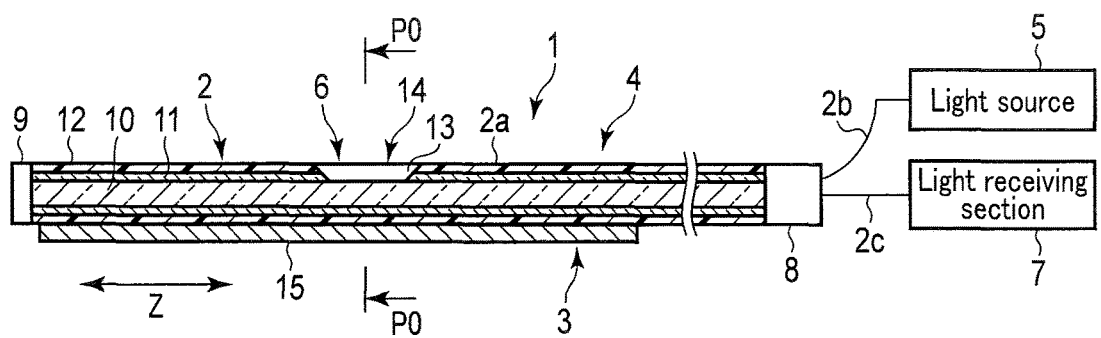
FIG. 1 is a longitudinal sectional view showing an outline configuration of an entire shape sensor according to a first embodiment of the present invention.
Figure 2:
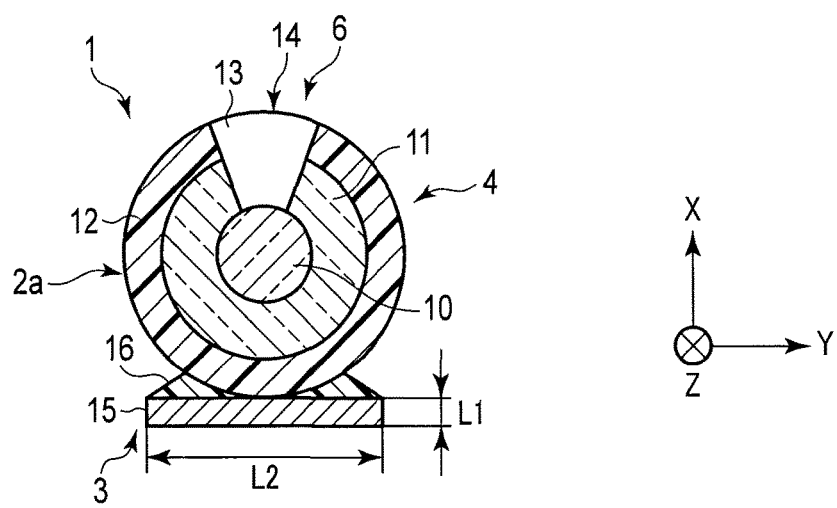
FIG. 2 is a cross-sectional view taken along a line P0-P0 depicted in FIG. 1.
Figure 3:
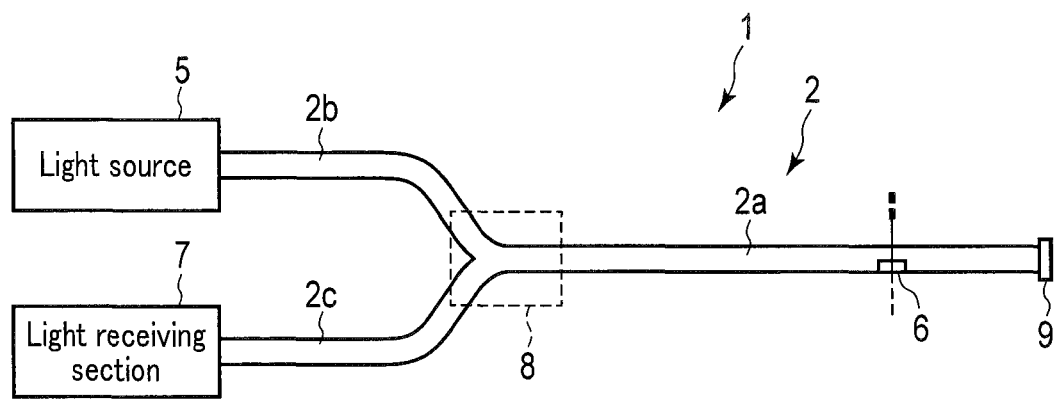
FIG. 3 is a schematic block diagram for explaining a principle of the shape sensor according to the first embodiment.
Figure 4:
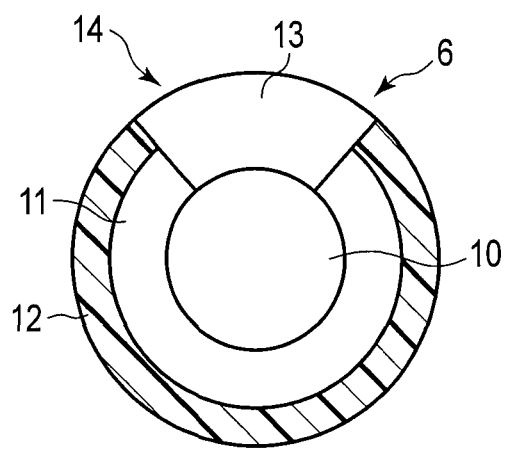
FIG. 4 is a transverse sectional view of a detection object section of the shape sensor in FIG. 3.

FIG. 1 is a longitudinal sectional view showing an outline configuration of an entire shape sensor 1 according to a first embodiment of the present invention, and FIG. 2 is a cross-sectional view taken along a line P0-P0 in FIG. 1. The shape sensor 1 according to this embodiment includes a shape sensor main body 4 that has one optical fiber 2 which can guide detection light having desired characteristics and a curving direction regulating section 3 which regulates a curvable direction of this optical fiber 2 to a desired direction. Further, FIG. 3 and FIG. 4 are schematic views for explaining a principle of the shape sensor 1.

The principle of the shape sensor 1 will be first described with reference to FIG. 3 and FIG. 4.

The shape sensor 1 is mainly constituted of a light source 5 that emits light, the optical fiber 2 that guides the light emitted from the light source 5, a detection object section 6, and a light receiving section (a light detecting section) 7 such as a light receiving sensor that detects the detection light propagated through the optical fiber 2. The light source 5 is, e.g., a light-emitting diode (LED) or a laser light source.

The optical fiber 2 has a Y-like shape forked into three directions by a coupling section (an optical coupler) 8, and one detection optical fiber 2a is bifurcated into two fibers, i.e., a light supply optical fiber 2b and a light reception optical fiber 2c.

A reflecting section 9 that reflects the guided light is provided at a distal end of the detection optical fiber 2. Here, as shown in FIG. 4, the optical fiber 2 is constituted of a core 10 and a cladding 11 that covers an outer periphery of the core 10. Furthermore, it may also have a covering member (a jacket) 12 as the outermost exterior.

The light supply optical fiber 2b is a light introduction path, and it guides the light emitted from the light source 5 provided at the end portion to the coupling section 8. The coupling section 8 has a function of guiding a great part of the light that has entered from the light source optical fiber 2b to the detection optical fiber 2a, and guiding at least a part of the light reflected by the reflecting section 9 to the light reception optical fiber 2c.

The shape sensor 1 according to this embodiment has the detection optical fiber 2a integrally mounted therein along a measurement target object, e.g., an elongated flexible curving structure, and detects a bent state and a bending direction of the flexible curving structure. Here, at the time of mounting the shape sensor 1 to the measurement target object, the shape sensor 1 can be disposed on an appropriate position of the measurement target object by positioning a bent portion of the measurement target object to the detection object section 6 of the shape sensor 1. The detection optical fiber 2a follows a flexible operation of the measurement target object, reflects the light that has entered from the light supply optical fiber 2b by the reflecting section 9 at the distal end, and allows the light to travel back and forth. That is, the light from the light supply optical fiber 2b via the coupling section 8 is guided to the reflecting section 9, and the light reflected by this reflecting section 9 is guided to return to the coupling section 8.

The light reception optical fiber 2c guides the light reflected by the reflecting section 9 and branched by the coupling section 8 to the light receiving section 7 provided at the end portion. The detection optical fiber 2a has at least one detection object section 6.

As shown in FIG. 4, the detection object section 6 has an opening portion 13 which is provided by removing a part of the cladding 11 from an outer periphery of the detection optical fiber 2a and through which a part of the core 10 is exposed, and an optical characteristic conversion member 14 arranged in the opening portion 13. It is to be noted that the detection object section 6 could enable the light passing through a light guide path to reach the opening portion 13 even if the core 10 is not exposed.

The optical characteristic conversion member 14 has a function of converting a characteristic of the guided light. The optical characteristic conversion member 14 is, e.g., a light guide loss member or a wavelength conversion member. For example, there is a light absorber as the light guide loss member, or there is a fluorescent material as the wavelength conversion member. In this embodiment, the optical characteristic conversion member is used as a light guide loss member.

The light emitted from the light source 5 is guided through the light supply optical fiber 2b, the coupling section 8, and the detection optical fiber 2a and reflected by the reflecting section 9 as an outward route. The reflected light is detection light, and it is branched in the coupling section 8, guided through the light reception optical fiber 2c, and reaches the light receiving section 7 as a return route. The light receiving section 7 photoelectrically converts the received detection lights, and outputs an electrical signal representing a light quantity.

In the shape sensor 1 having the above-described configuration, when the light guided through the optical fiber 2 enters the optical characteristic conversion member 14, a loss is produced. This light guide loss amount varies depending on the direction of bending and oscillation and a bending amount of the light reception optical fiber 2c. Even if the detection optical fiber 2a is linear, a given light quantity is lost in the optical characteristic conversion member 14 in accordance with a width of the opening portion 13.

Assuming that this light loss amount is used as a reference, for example, if the optical characteristic conversion member 14 is arranged on an outer peripheral surface of the bending detection optical fiber 2a in a bending direction, a larger light guide loss amount than the reference light guide loss amount is produced. In contrast, if the optical characteristic conversion member 14 is arranged on an inner peripheral surface of the bending detection optical fiber 2a in the bending direction, a smaller light guide loss amount than the reference light guide loss amount is produced. This change in light guide loss amount is reflected in an amount of detection light received by the light receiving section 7. That is, it is reflected in an output signal from the light receiving section 7.

Thus, a bending direction and a bending amount (angle) at a position of the detection object section 6 of the shape sensor 1, i.e., a position on the measurement target object where the optical characteristic conversion member 14 is provided can be detected by using the output signal from the light receiving section 7. Furthermore, the curving direction regulating section 3 has a substantially tabular core member 15 displaced on at least a part of the shape sensor main body 4, e.g., the detection optical fiber 2a along a light propagating direction of the optical fiber 2.

This core member 15 is formed of an elastic member made of a metal or a resin. As the metal elastic member, for example, a spring single-core steel wire or a leaf spring member (SUS) is preferred. Moreover, as the resin elastic member, polycarbonate, polyacetal, or PEEK is preferred.

The core member 15 is bonded and fixed on a side surface of the outer peripheral surface of the detection optical fiber 2a on the opposite side of a direction of the detection object section 6 by a bonding member 16. As the bonding member 16, for example, an elastic adhesive of epoxy or a silicon resin is preferred. Here, the bonding member 16 may be continuously applied over an overall length of the optical fiber 2 in an axial direction or may be discontinuously applied (spotted) at desired intervals.

This core member 15 is formed to have a cross-sectional structure such that a cross-sectional shape in a planar direction orthogonal to the axial direction of the optical fiber (the light propagating direction) is a planar shape that enhances bending rigidity in a specific direction. Here, in FIG. 2, the axial direction of the optical fiber 2 (the light propagating direction) is a Z axis direction, a direction of the detection object section 6 in a plane orthogonal to this Z axis is an X axis direction, and a direction orthogonal to the X axis is a Y axis direction. In the example shown in FIG. 2, the cross-sectional structure of the core member 15 is formed into a rectangle having a short length L1 in the X axis direction and a long length L2 in the Y axis direction.

The shape sensor 1 can easily bend in a periaxial direction of the Y axis (the periaxial direction means a circling direction orthogonal to the axis hereinafter) but hardly bends in a periaxial direction of the X axis due to the tabular shape, and its main curvable direction is regulated. That is, the shape sensor 1 can readily bend on a long side of the core member 15, but hardly bends on a short side of the same.

In this embodiment, a direction of the detection object section 6 of the shape sensor 1 is a detection sensitivity direction, and the detection optical fiber 2a of the optical fiber 2 is disposed so that the direction of the detection object section 6 of this shape sensor 1 coincides with the Y axis. In this state, the optical fiber 2 and the core member 15 can be readily curved in the periaxial direction of the Y axis. Thus, it is desirable to fix the detection optical fiber 2a to the core member 15 so that the detection object section 6 having directivity to the curving direction can oscillate in a flexible direction (the X direction) of the core member 15.

Moreover, the shape sensor 1 according to this embodiment has the detection optical fiber 2a integrally mounted to become parallel to a longitudinal direction of a (non-illustrated) measurement target object (e.g., an inserting section main body including a curving section of an endoscope) that is long and has flexibility, thereby detecting a bent state and a bending direction of the measurement target object.

At the time of mounting the shape sensor 1 to the measurement target object, when positioning is performed so that the detection object section 6 of the detection optical fiber 2a is applied to a bent portion of the measurement target object, the detection object section 6 is disposed at an appropriate position on the measurement target object. For example, in this embodiment, at least a part of the shape sensor 1 is bonded and fixed to a channel arranged in a flexible curving structure by, e.g., an adhesive.

A function of the shape sensor 1 according to this embodiment having the above-described configuration will now be described.

As to this shape sensor 1, an integrally mounted measurement target object (not shown) curves, and the shape sensor 1 also curves upon receiving an external force provided by this curving. As described above, in FIG. 2, the shape sensor 1 easily bends in the X direction (a rotating direction with the Y axis at the rotation center) on the long side of the core member 15 but is hard to bend in the Y direction (a rotating direction with the X axis at the rotation center) on the short side of the same, which is curving that gives priority to one axis.

Further, when the shape sensor 1 curves, a light quantity of the detection light leaking to the outside from a direction of the detection object section 6 changes due to its curvature. Thus, with the change in leaking light quantity, a light quantity of the detection light that reaches the light receiving section 7 also changes, and a measurement value to be output also varies. At this time, as the curvature of the shape sensor 1 is increased, a return light quantity of the detection light from the detection optical fiber 2a greatly varies. Furthermore, the return light quantity changes to increase when the detection object section 6 of the detection optical fiber 2a curves in a compressing direction (in FIG. 1, when the detection optical fiber 2a curves into a downwardly curved shape), or the return light quantity changes to decrease when the detection object section 6 of the detection optical fiber 2a curves in a pulling direction (in FIG. 1, when the detection optical fiber 2a curves into an upwardly curved shape).

The above-described shape sensor 1 according to this embodiment exercises the following effect.

The shape sensor 1 according to this embodiment includes the curving direction regulating section 3 that regulates the optical fiber 2 to hardly curve in a desired direction on at least a part of the optical fiber 2, e.g., the detection optical fiber 2a along the optical axis direction. Since this curving direction regulating section 3 is included, it is possible to provide the shape sensor 1 that is hardly affected by, e.g., torsion due to an external force other than in a one axis direction along which the sensor can easily bend and that can measure a curved shape in a desired curving direction alone.

Thus, even if the shape sensor 1 is disposed and fixed to the measurement target object at few holding points such as a front end or a rear end, the shape sensor 1 is hardly distorted, can curve in a desired curving direction only, and can precisely measure a curved shape. It is to be noted that the example where the cross-sectional structure of the core member 15 is formed into a rectangular shape has been described in this embodiment, but the cross-sectional structure of the core member 15 may have an elliptic cross-sectional shape.

[Second Embodiment]

Figure 5A:
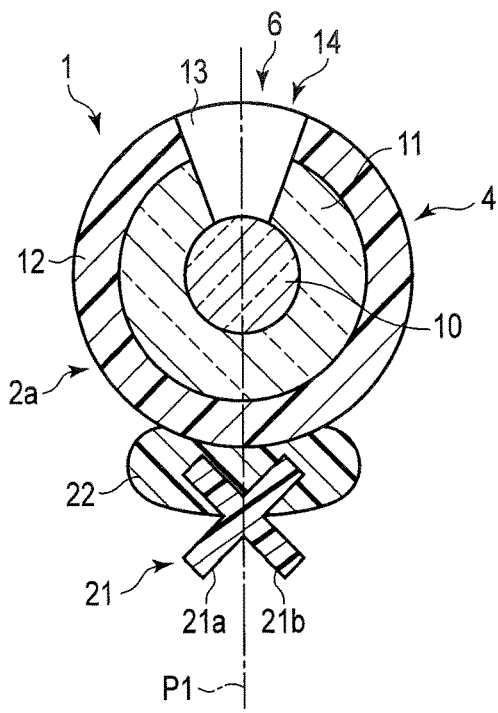
FIG. 5A is a transverse sectional view of a detection object section of a shape sensor according to a second embodiment of the present invention taken along a line P1-P1.

A shape sensor 1 according to a second embodiment will now be described. FIG. 5A is a transverse sectional view of a detection object section of a shape sensor according to the second embodiment of the present invention taken along a line P1-P1.

This embodiment is a modification of the curving direction regulating section 3 of the shape sensor 1 according to the first embodiment (see FIG. 1 and FIG. 2). It is to be noted that parts other than a modified part are the same as those in the first embodiment, and like reference numerals denote constituent parts in FIG. 5A equal to those in FIG. 1 and FIG. 2 to omit a description thereof.

In the shape sensor 1 according to this embodiment, as shown in FIG. 5A, as a curving direction regulating section 3, a core member 21 having an X-like cross-sectional shape in a direction vertical to a light propagating direction of an optical fiber 2 is provided. This core member 21 is integrally made of, e.g., a synthetic resin material. As a cross-sectional structure of the core member 21 according to this embodiment, there are two planes forming an X-like shape (a first plane 21a and a second plane 21b) orthogonal to each other at 90°, and bending rigidity is strong in respective planar directions of the first plane 21a and the second plane 21b, but the bending rigidity is weak in a direction dividing an angle between the first plane 21a and the second plane 21b into two (a direction of a reference line P1 indicted by an alternate long and short dash line in FIG. 5A (an X axis direction)).

The core member 21 is bonded and fixed to a side surface of an outer peripheral surface of a detection optical fiber 2a on the opposite side of a direction of a detection object section 6 by a bonding member 22 such as an adhesive. At the time of bonding and fixing this core member 21, positioning and fixation are carried out in a state that a direction of the reference line P1 dividing the angle between the first plane 21a and the second plane 21b of the core member 21 into two is positioned in a direction toward the detection object section 6. Consequently, the core member 21 has the cross-sectional structure that the cross-sectional shape in the direction vertical to the light propagating direction of the optical fiber 2 is a shape that enhances the bending rigidity in a specific direction.

A function and an effect of the shape sensor 1 according to the present invention will now be described.

The curving direction regulating section 3 of the shape sensor 1 has the configuration that the core member 21 having the X-like cross-sectional structure is provided and the bending rigidity is strong in the respective planar directions of the first plane 21*a* and the second plane 21*b* forming the X-like shape. Furthermore, it also has the configuration that the rigidity is weak in the direction dividing the angle between the first plane 21*a* and the second plane 21*b* into two (an extending direction of the alternate long and short dash line of the reference line P1 shown in FIG. 5A). Thus, a main curvable direction of the shape sensor 1 is regulated like the first embodiment, and the shape sensor 1 that is hardly affected by, e.g., torsion and can measure a curved shape in a desired curving direction can be provided.

[Third Embodiment]

A shape sensor 1 according to a third embodiment will now be described.

Figure 5B:
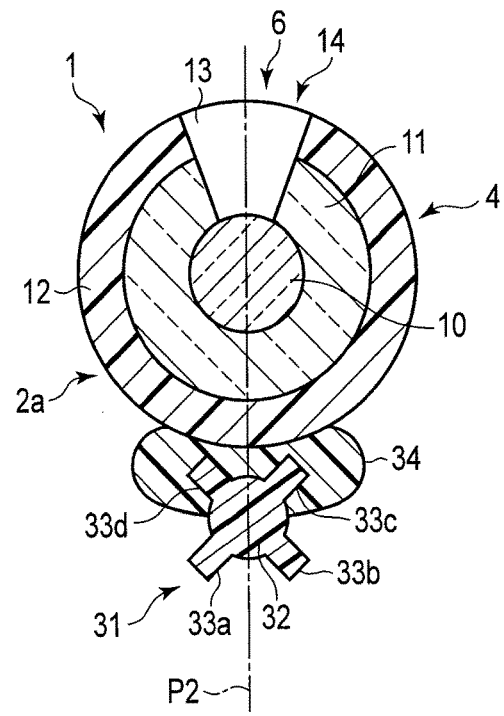
FIG. 5B is a transverse sectional view of a detection object section of a shape sensor according to a third embodiment of the present invention taken along a line P2-P2.

FIG. 5B is a transverse sectional view of a detection object section of a shape sensor according to the third embodiment taken along a line P2-P2. This embodiment is a modification of the curving direction regulating section 3 of the shape sensor 1 according to the first embodiment (see FIG. 1 and FIG. 2). It is to be noted that parts other than a modified part are the same as those in the first embodiment, and like reference numerals denote constituent parts in FIG. 5B equal to those in FIG. 1 and FIG. 2 to omit a description thereof.

In the shape sensor 1 according to this embodiment, as a curving direction regulating section 3, a core member 31 having a cross-sectional structure shown in FIG. 5B is provided. The cross-sectional structure of the core member 31 according to the present invention is a structure in which four outwardly protruding ribs 33*a*, 33*b*, 33*c*, and 33*d* are allocated on an outer periphery of a center member 32 having a circular cross-sectional shape at equal angles of 90°. This core member 31 is integrally molded by using, e.g., a synthetic resin material.

The cross-sectional structure of the core member 31 according to this embodiment has a first planar direction connecting the two ribs 33*a* and 33*c* arranged at positions of 180° in the four ribs 33*a*, 33*b*, 33*c*, and 33*d* allocated at equal angles of 90° and a second planar direction connecting the ribs 33*b* and 33*d* in the same. The respective first planar direction and second planar direction are configured to have strong bending rigidity in the planar directions. Moreover, a direction dividing an angle between the first planar direction and the second planar direction into two (a direction of a reference line P2 indicated by an alternate long and short dash line in FIG. 5B (an X axis direction)) is configured to have weak bending rigidity.

The core member 31 is bonded and fixed on a side surface of an outer peripheral surface of a detection optical fiber 2*a* on the opposite side of a direction of a detection object section 6 by a bonding member 34 such as an adhesive. At the time of bonding and fixing this core member 21, positioning and fixation are carried out in a state that a direction of the reference line P1 dividing the angle between the first plane 21*a* and the second plane 21*b* of the core member 21 into two is positioned in a direction toward the detection object section 6. Consequently, the core member 21 has the cross-sectional structure that the cross-sectional shape in the direction vertical to the light propagating direction of the optical fiber 2 is a shape that enhances the bending rigidity in a specific direction.

A function and an effect of the shape sensor 1 according to the present invention will now be described.

The curving direction regulating section 3 of the shape sensor 1 has the configuration that the core member 31 having the cross-sectional structure shown in FIG. 5B is provided, the first planar direction connecting the two ribs 33*a* and 33*b* arranged at positions of 180° and the second planar direction connecting the ribs 33*b* and 33*d* are included, and the respective planar directions have the strong bending rigidity. Additionally, the direction dividing the angle between the first planar direction and the second planar direction into two (the direction of the reference line P2 indicated by the alternate long and short dash line in FIG. 5B (the X axis direction)) is configured to have the weak bending rigidity. Thus, like the above-described first embodiment, a main curvable direction of the shape sensor 1 is regulated, and the shape sensor 1 that is hardly affected by, e.g., distortion and can measure a curved shape in a desired curving direction alone can be provided.

[Fourth Embodiment]

A shape sensor 41 according to a fourth embodiment of the present invention will now be described.

FIG. 6 is a longitudinal cross-sectional view showing an outline configuration of an entire shape sensor 41 according to the fourth embodiment, and FIG. 7 is a cross-sectional view taken along a line P3-P3 in FIG. 6. In the shape sensor 41 according to this embodiment, as shown in FIG. 7, there is provided a shape sensor main body 44 having, e.g., four optical fibers 42 (42*a*, 42*b*, 42*c*, and 42*d*) and multiple, e.g., three substantially discoid fiber holding members 43 that hold the four optical fibers 42*a* to 42*d* aligned in parallel. It is to be noted that the four optical fibers 42*a* to 42*d* are equivalent to the detection optical fiber 2*a* according to the first embodiment (see FIG. 1 and FIG. 2), and like reference numerals denote constituent parts shown in FIG. 6 and FIG. 7 equal to those in FIG. 1 and FIG. 2 to omit a description thereof.

The fiber holding members 43 are aligned along a light propagating direction of an optical fiber at appropriate intervals. In each fiber holding member 43, fiber insertion holes (fiber holding sections) 44*a* to 44*d* formed of circular holes are formed on the top, bottom, left, and right of a center point O in FIG. 7, respectively.

The respective fiber insertion holes 44*a* to 44*d* are arranged at equal intervals. The four optical fibers 42*a* to 42*d* are inserted into these fiber insertion holes 44*a* to 44*d* and fixed in this state. Consequently, the four optical fibers 42*a* to 42*d* are held without coming into contact with each other.

Further, each detection object section 6 of the four optical fibers 42*a* to 42*d* is arranged between two fiber holding members 43 as shown in FIG. 6. Here, in FIG. 7, the detection object sections 6 of the optical fiber 42*a* at an upper position and the optical fiber 42*c* at a left position are arranged to face upward, and the detection object sections 6 of the optical fiber 42*b* at a lower position and the optical fiber 42*d* at a right position are arranged to face downward.

Furthermore, a curving direction regulating section 45 that regulates curvable directions of the optical fibers 42*a* to 42*d* to desired directions is provided to the shape sensor main body 44 at a lower end portion of each fiber holder member 43 in FIG. 7. The curving direction regulating section 45 has a substantially tabular core member 46 arranged to be parallel to the light propagating directions of the respective optical fibers 42a to 42d.

The tabular core member 46 is arranged on or near outer peripheries of the respective fiber holding members 43 of the shape sensor main body 44, and bonded and fixed to outer peripheral surfaces of the respective fiber holding members 43 by a bonding member 47 such as an adhesive. It is to be noted that the core member 46 may be configured to be screwed to the outer peripheral surfaces of the respective fiber holding members 43 of the shape sensor main body 44.

The optical fibers 42a to 42d are arranged in a maximum circumscribed circle 48 defined by the outermost peripheral portion of the tabular core member 46. Moreover, in this embodiment, the example where the number of the optical fibers 42 incorporated in the shape sensor main body 44 is four and the number of the fiber holding members 43 is three has been described, but these numbers can be changed as required without being restricted.

Additionally, in the shape sensor 41 according to this embodiment, the shape sensor main body 44 is integrally mounted along a non-illustrated measurement target object which is, e.g., an elongated flexible member. At this time, when a bent portion of the measurement target object is positioned to be applied to the detection object sections 6 of the respective optical fibers 42a to 42d, the detection object sections 6 of the respective optical fibers 42a to 42d are disposed at appropriate positions on the measurement target object.

In this state, light emitted from a light source 5 of the respective optical fibers 42a to 42d is guided through a light supply optical fiber 2b, a coupling section 8, and a detection optical fiber 2a and reflected by a reflecting section 9 as an outward route. The light reflected by the reflecting section 9 turns to detection light, and is branched in the coupling section 8, guided through a light reception optical fiber 2c, and reaches the light receiving section 7 as a return route. The light receiving section 7 photoelectrically converts the received detection light, and outputs an electrical signal representing a light quantity. Consequently, a bent state and a bending direction of the measurement target object are detected.

A function and an effect of this embodiment will now be described.

In the shape sensor 41 according to this embodiment, when a non-illustrated measurement target object curves, the shape sensor 41 disposed in the measurement target object receives external force from the measurement target object and curves. At this time, the shape sensor 41 can easily curve in a periaxial direction of a Y axis shown in FIG. 7 but is hard to curve in a periaxial direction of an X axis due to the cross-sectional shape of the core member 46. Thus, as shown in FIG. 7, an X axis direction component of the external force enables the shape sensor 41 to curve, which is curving that gives priority to one axis with the Y axis at the rotation center in a coordinate system.

Further, when the shape sensor 41 curves, a light quantity of the detection light leaking to the outside from directions of the detection object sections 6 of the respective optical fibers 42a to 42d changes due to a curvature. Therefore, with this change in leaking light quantity, a light quantity of the detection light that reaches the light receiving section 7 also changes, and a measurement value to be output also varies. At this time, as the curvature of the shape sensor 41 is increased, a return light quantity of the detection light from the detection optical fiber 2a greatly varies.

Furthermore, when the detection object section 6 of the detection optical fiber 2a curves in a compressing direction (in FIG. 6, when the respective optical fibers 42a to 42d curve into downwardly curved shapes), the return light quantities change to increase in the optical fiber 42a at the upper position and the optical fiber 42c at the left position in FIG. 7. On the other hand, the return light quantities change to decrease in the optical fiber 42b at the lower position and the optical fiber 42d at the right position.

Moreover, when the detection object section 6 of the detection optical fiber 2a curves in the compressing direction (when the respective optical fibers 42a to 42d shown in FIG. 7 curve in the X direction), the return light quantities change to decrease in the optical fiber 42a at the upper position and the optical fiber 42c at the left position, and the return light quantities change to increase in the optical fiber 42b at the lower position and the optical fiber 42d at the right position.

As described above, in the shape sensor 41 according to this embodiment, the curving direction regulating section 45 that regulates curvable directions of the optical fibers 42a to 42d to desired directions is provided at the lower end portions of the respective fiber holding members 43 of the shape sensor main body 44, and this curving direction regulating section 45 is formed of the substantially tabular core member 46 installed to be parallel to the light propagating directions of the respective optical fibers 42a to 42d.

With the use of this core member 46, the shape sensor 41 can easily bend in the X direction shown in FIG. 7 but is hard to bend in the Y direction by the curving direction regulating section 45, and bending except for one direction is regulated. Thus, like the first embodiment, it is possible to provide the shape sensor 41 that is hardly affected by, e.g., distortion and can measure a curved shape in a desired curving direction alone.

Additionally, in the shape sensor 41 according to this embodiment, since the optical fibers 42a to 42d can be disposed in one shape sensor main body 44, a curved shape of the non-illustrated measurement target object can be measured at multiple positions in addition to the effect of the first embodiment. It is to be noted that the shape sensor having many detection points in the axial direction by moving the positions of the detection object sections 6 of the optical fibers 42a to 42d in the axial direction can be provided.

[Fifth Embodiment]

Figure 8:
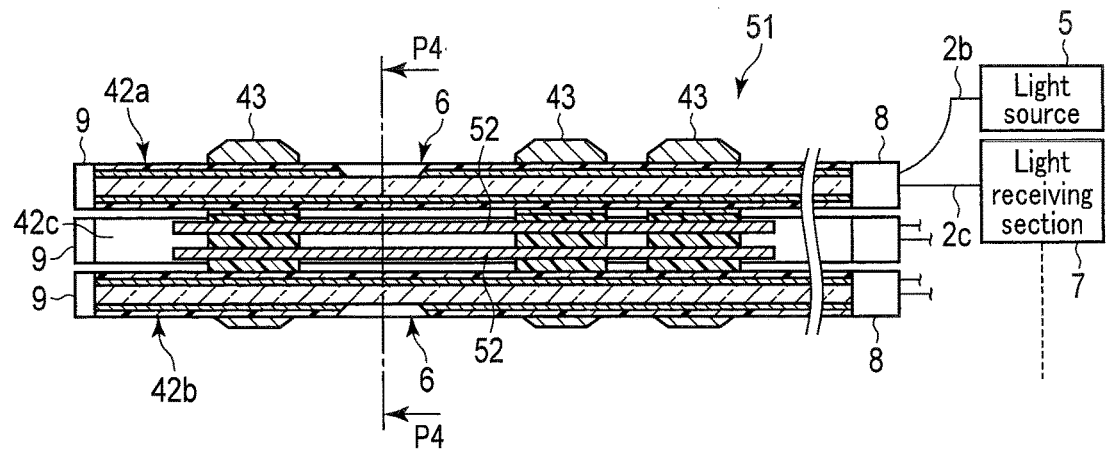
FIG. 8 is a longitudinal sectional view showing an outline configuration of an entire shape sensor according to a fifth embodiment of the present invention.

A shape sensor 51 according to a fifth embodiment of the present invention will now be described with reference to FIG. 8 and FIG. 9. FIG. 8 is a longitudinal sectional view showing an outline configuration of an entire shape sensor according to the fifth embodiment of the present invention, and FIG. 9 is a cross-sectional view taken along a line P4-P4 depicted in FIG. 8.

This embodiment is a modification of the curving direction regulating section 45 of the shape sensor 41 according to the fourth embodiment (see FIG. 6 and FIG. 7). It is to be noted that parts other than a modified part are the same as those in the fourth embodiment, and like reference numerals denote constituent parts which are shown in FIG. 8 and FIG. 9 and equal to those in FIG. 6 and FIG. 7 to omit a description thereof.

Figure 9:
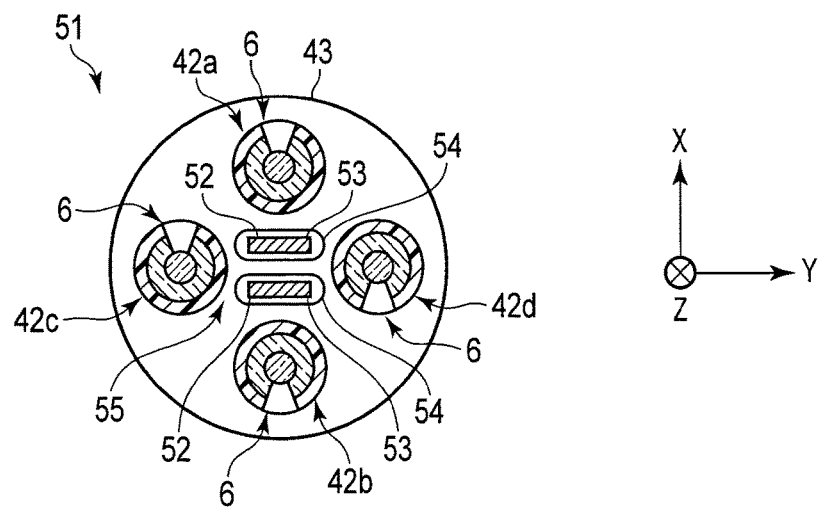
FIG. 9 is a cross-sectional view taken along a line P4-P4 depicted in FIG. 8.

In the shape sensor 51 according to this embodiment, two core material insertion holes (core material holding sections) 53 into which two tabular core materials 52 are inserted respectively are provided in an inner portion of fiber insertion holes 44a to 44d of each fiber holding member 43 as shown in FIG. 9. The two core materials 52 are arranged to be aligned parallel to a Y axis direction in FIG. 9. The two core materials 52 inserted into the two core material insertion holes 53 respectively are bonded by bonding members 54, e.g., an adhesive. It is to be noted that the two core materials 52 may be held by a holding and fixing method using no bonding member, e.g., fusion of the fiber holding member 43, press fitting (in this case, a hole diameter of each core material insertion hole 53 is slightly smaller than a radial cross-sectional shape of the core material 52), screwing, or the like.

Further, in this embodiment, the two aligned core members 52 form a core member 55 constituting a curving direction regulating section 3 that regulates curvable directions of optical fibers 42a to 42d to desired directions. In this case, a bending rigidity of the core member 55 is weak in a direction along which the core materials 52 are aligned (an X direction), and the bending rigidity is strong in a direction orthogonal to the aligning direction of the core materials 52 (a Y direction). It is to be noted that the number of the core materials 52 is not restricted to two, and may be one, three, or more.

Furthermore, a position of each core material insertion hole 53 is not restricted to the vicinity of the center of each fiber holding member 43, and may be, e.g., on the same axes as the optical fibers 42a to 42d or the outside of the optical fibers 42a to 42d as long as it is provided within the fiber holding member 43.

Moreover, a method of mounting the shape sensor 51 according to this embodiment to a non-illustrated measurement target object is the same as that of the shape sensor 41 according to the fourth embodiment. Additionally, detection object sections 6 of the respective optical fibers 42a to 42d are disposed at appropriate positions on a measurement target object by positioning a bent portion of the measurement target object to the detection object sections 6 of the respective optical fibers 42a to 42d. Consequently, a bent state and a bending direction of the measurement target object are detected.

A function and an effect of this embodiment will now be described.

The shape sensor 51 according to this embodiment detects a bent state and a bending direction of the measurement target object like the shape sensor 41 according to the fourth embodiment. In the shape sensor 51, the two tabular core materials 52 are arranged in parallel in an inside portion of the fiber insertion holes 44a to 44d of each fiber holding member 43. Further, a main curvable direction of the shape sensor 51 is regulated by the core member 55 constituted of the two tabular core materials 52 in a state that the shape sensor 51 can readily bend in the X direction and a periaxial direction of a Y axis but is hard to bend in a periaxial direction of an X axis. Thus, it is possible to provide the shape sensor 51 that is hardly affected by distortion or the like and can measure a curved shape in a desired curving direction alone like the first embodiment.

Furthermore, in the shape sensor 51 according to this embodiment, since the core member 55 constituted of the two tabular core materials 52 is arranged in the inside portion of the fiber insertion holes 44a to 44d of each fiber holding member 43, an effect of reducing a diameter of the shape sensor 51 can be provided as compared with a case where the core member 46 is mounted on the outer peripheral surface of each fiber holding member 43.

[Sixth Embodiment]

Figure 10:
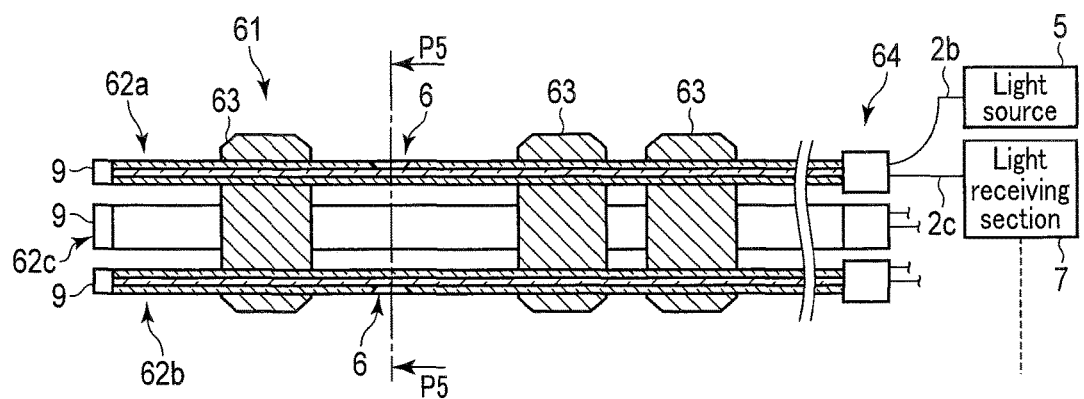
FIG. 10 is a longitudinal sectional view showing an outline configuration of an entire shape sensor according to a sixth embodiment of the present invention.

A shape sensor 61 according to a sixth embodiment of the present invention will now be described with reference to FIG. 10 and FIG. 11. FIG. 10 is a longitudinal sectional view showing an outline configuration of the entire shape sensor 61 according to the sixth embodiment, and FIG. 11 shows a cross-sectional view taken along a line P5-P5 in FIG. 10.

Figure 11:
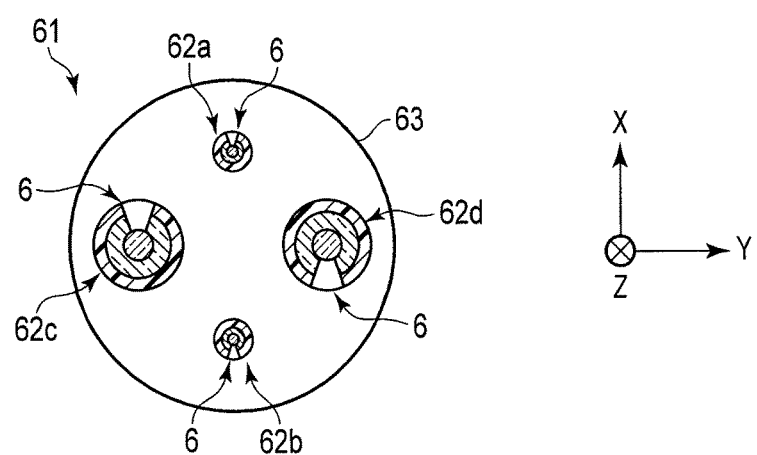
FIG. 11 is a cross-sectional view taken along a line P5-P5 depicted in FIG. 10.

In the shape sensor 61 according to this embodiment is provided a shape sensor main body 64 that has multiple, four in this embodiment as shown in FIG. 11, optical fibers 62 (62a, 62b, 62c, and 62d) and multiple, three in this embodiment, substantially discoid fiber holding members 63 that hold the four optical fibers 62a to 62d aligned in parallel. It is to be noted that the four optical fibers 62a to 62d have the same configuration as the detection optical fiber 2a according to the first embodiment (see FIG. 1 and FIG. 2), respectively. Thus, in FIG. 10 and FIG. 11, like reference numerals denote parts equal to those in FIG. 1 and FIG. 2 to omit a description thereof.

In the shape sensor 61 according to this embodiment, as the four optical fibers 62a to 62d, two types of optical fibers having different bending rigidities are used. Here, the two optical fibers 62a and 62b vertically arranged in FIG. 1 have narrower outer diameters and lower bending rigidities than the two horizontally arranged optical fibers 62c and 62d. Thus, the bending rigidity of the entire shape sensor main body 64 is greatly affected by the two horizontally arranged optical fibers 62c and 62d having the high bending rigidities. Thus, the two optical fibers 62c and 62d horizontally arranged in FIG. 11 have functions corresponding to the core member 46 in the shape sensor 41 according to the fourth embodiment (see FIG. 6 and FIG. 7) and the core member 55 of the shape sensor 51 according to the fifth embodiment (see FIG. 8 and FIG. 9).

Therefore, the shape sensor main body 64 according to this embodiment can easily curve in a periaxial direction of a Y axis shown in FIG. 11 but is hard to curve in a periaxial direction of an X axis. Thus, as shown in FIG. 11, the shape sensor 61 can curve by an X axis direction component of an external force, which is curving giving priority to one axis with the Y axis at a rotation center in a coordinate system.

It is to be noted that, in this embodiment, the description has been given as to the example where thicknesses of the two optical fibers 62c and 62d horizontally arranged in FIG. 11 and the two optical fibers 62a and 62b vertically arranged in FIG. 11 are changed to provide the bending rigidity with directivity. The levels of the bending rigidity may be changed to provide the bending rigidities of the optical fibers with the directivity by differentiating a diameter of at least one constituent element of four constituent elements, i.e., a core, a cladding, a coat, and a jacket of each optical fiber.

Moreover, the directivity may be provided to the bending rigidity by changing a material of the core or the jacket constituting each optical fiber (for example, changing the material of the core to a combination of quartz glass and a resin or changing the material of the jacket to a combination of a fluorine resin and a polyimide resin). Additionally, the directivity may be provided to the bending rigidity by using a combination of a diameter and a material. Further, in the shape sensor 61 according to this embodiment, metallic spring materials each having an isotropically circular cross-sectional shape may be adopted in place of the two optical fibers 62c and 62d horizontally arranged in FIG. 11.

A function and an effect of this embodiment will now be described.

In the shape sensor 61 according to this embodiment, when the two types of optical fibers having different bending rigidities are used as the four optical fibers 62a to 62d incorporated in the shape sensor main body 64, the two optical fibers 62c and 62d horizontally arranged in FIG. 11 can provide the functions corresponding to the core member 46 in the shape sensor 41 according to the fourth embodiment (see FIG. 6 and FIG. 7) and the core member 55 in the shape sensor 51 according to the fifth embodiment (see FIG. 8 and FIG. 9). Thus, the shape sensor 61 according to this embodiment can provide the same function and effect as those of the shape sensor 1 according to the first embodiment. Additionally, in the shape sensor 61 according to this embodiment, since core materials other than the optical fibers do not have to be used, besides the effect of the first embodiment, component costs or assembling costs can be decreased as compared with the shape sensor 41 according to the fourth embedment or the shape sensor 51 according to the fifth embodiment, and a more inexpensive shape sensor can be provided.

[Seventh Embodiment]

A shape sensor 73 according to a seventh embodiment of the present invention will now be described with reference to FIG. 12 and FIG. 13. This embodiment has a configuration such that a shape sensor 73 is mounted in a distal end insertion tube 72 of an endoscope 71 which is a measurement target object to measure a curved shape of the distal end insertion tube 72.

Figure 12:
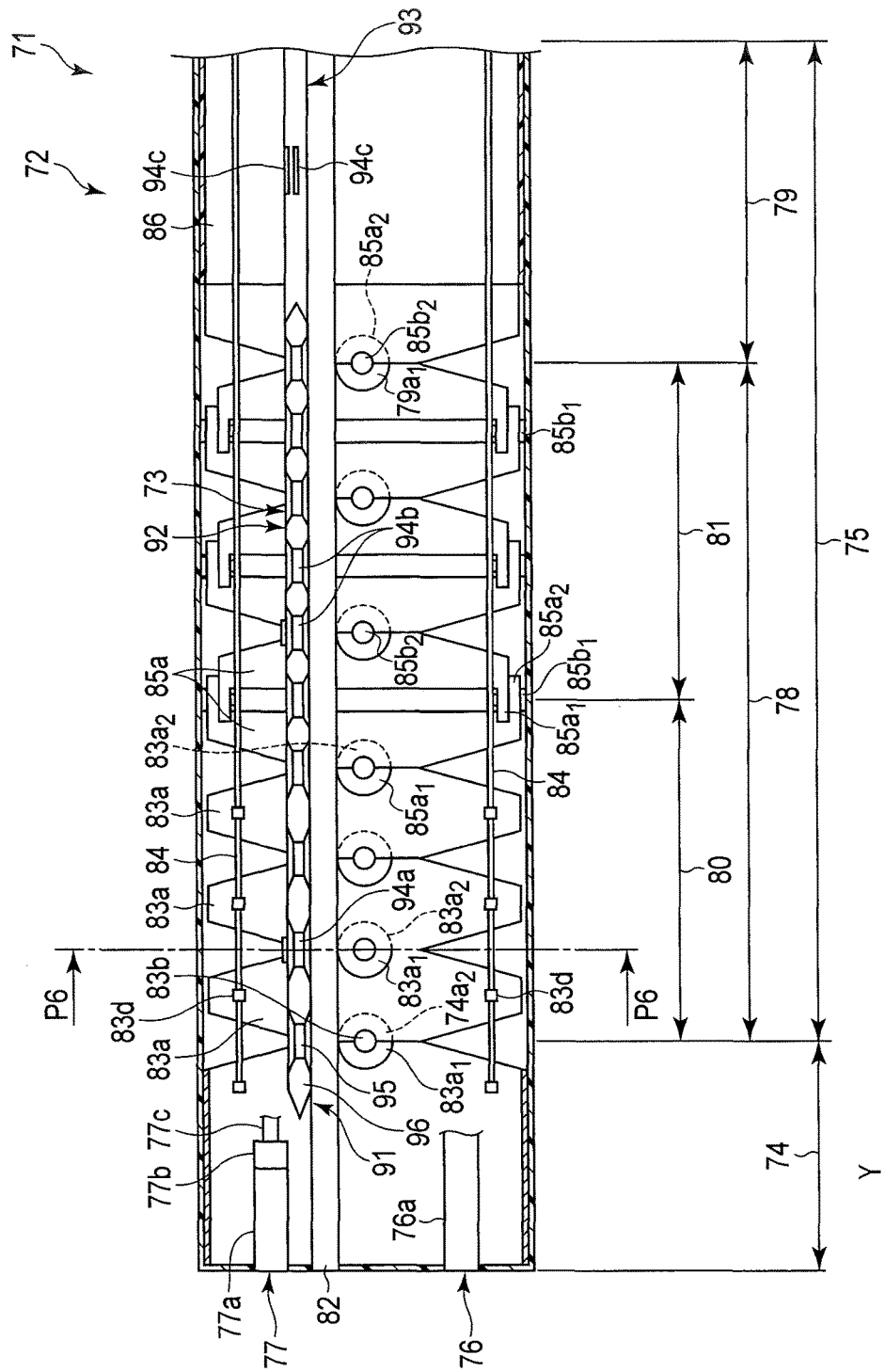
FIG. 12 is a longitudinal sectional view showing an internal configuration of a distal end part of a distal end insertion tube of an endoscope according to a seventh embodiment of the present invention.
Figure 13:
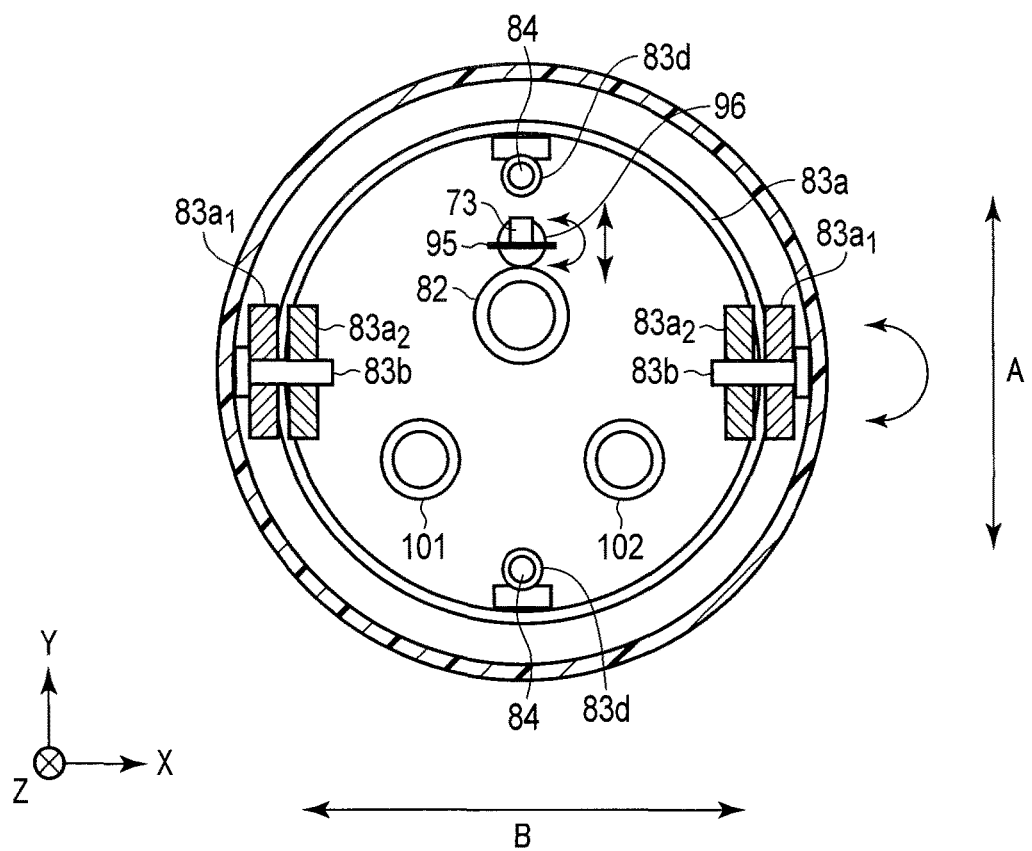
FIG. 13 is a cross-sectional view taken along a line P6-P6 depicted in FIG. 12.

FIG. 12 is a longitudinal cross-sectional view showing an internal configuration of a distal end part of the distal end insertion tube 72 of the endoscope 71, and FIG. 13 is a cross-sectional view taken along a line P6-P6 in FIG. 12.

A configuration of the distal end insertion tube 72 of the endoscope 71 will be described first.

The distal end insertion tube 72 is constituted of a hard distal end section 74 and a flexible curving structure 75. The flexible curving structure 75 is a curving direction regulating section with a curving directivity, including a curving easiness by which curving in a specific direction other than a center line direction (a Z axis direction in FIG. 12) is easy, and a curving difficulty by which curving in any other direction is difficult.

As shown in FIG. 12, an illuminating section 76 and an observing section 77 are provided in the distal end section 74. A light guide 76a is provided to the illuminating section 76. A proximal end portion of this light guide 76a is extended to a connector section side of a non-illustrated universal cord.

Further, when the connector section is connected to a light source apparatus, illumination light emitted from the light source apparatus is supplied to the illuminating section 76 through the light guide 76a, and applied to the outside. An objective optical system 77a and an image sensor 77b are provided to the observing section 77.

An endoscope observation image of an observation target formed by an imaging optical system is photoelectrically converted by the image sensor 77b, and an image signal is generated. The image signal is transmitted to a non-illustrated video processor side through a signal line 77c, and the endoscope observation image is displayed in a non-illustrated monitor.

A flexible curving structure 75 is constituted of a curving regulating section 78 and a free curving section 79. The curving regulating section 78 is formed of an operation curving section 80 and a second curving section 81. The operation curving section 80 is formed of a two-direction curving section that can curve in two directions, e.g., up and down directions (up-down) of the endoscope 71. The second curving section 81 is formed of a four-direction curving section that can curve in four directions, e.g., up and down directions (up-down) and left and right directions (left-right) of the endoscope 71.

The curving regulating section 78 can curve in desired two directions (up-down) at a desired curvature by an operation of a dial such as a non-illustrated curving operation knob provided on a non-illustrated hand operating section of the endoscope 71.

An internal configuration of the distal end insertion tube 72 will now be described with reference to FIG. 12. The illuminating section 76, the observing section 77, a treatment tool insertion channel 84 into which a non-illustrated treatment tool or the like can be inserted, a non-illustrated air supply/water supply nozzle, a non-illustrated jet water supply opening portion, and others are arranged in the distal end section 74. A distal end portion of the operation curving section 80 is coupled with a rear end side of the distal end section 74.

The operation curving section 80 is a coupling structure of curving piece members 83a having ring-shaped curving piece members 83a coupled along a center line direction (a Z axis direction in FIG. 12) of the flexible curving structure 75. A pair of tongue-shaped frontward protruding portions 83a1 protruding frontward are formed at a front end portion of each curving piece member 83a, and a pair of tongue-shaped rearward protruding portions 83a2 protruding rearward are formed at a rear end portion of the same. The pair of frontward protruding portions 83a1 are arranged at positions apart from each other at 180° in a circumferential direction of each curving piece member 83a. The pair of rearward protruding portions 83a2 are likewise arranged at positions apart from each other at 180° in the circumferential direction of each curving piece member 83a.

Moreover, the pair of frontward protruding portions 83a1 and the pair of rearward protruding portions 83a2 of each curving piece member 83a are arranged at positions corresponding to front and rear directions (the same positions in the circumferential direction of each curving piece member 83a). As shown in FIG. 13, a turning shaft 83b such as a hinge pin or a rivet for curving in up and down directions is inserted into each of portions (two positions) where the rearward protruding portion 83a of the front curving piece member 83a overlaps the frontward protruding portion 83a1 of the adjacent rear curving piece member 83a. Thus, the front and rear curving piece members 83a are coupled with each other to allow their turning motion around each turning shaft 83b in one direction only (around an X axis in FIG. 12 and FIG. 13).

With such a coupling structure allowing the turning motion, the operation curving section 80 regulates a curving easy direction to only one direction, which is a periaxial direction of a center line of the flexible curving structure 75, as indicated by an arrow A in FIG. 13, thereby forming a one-direction curving regulating section that can curve in two directions, i.e., up and down directions (up-down) of the endoscope 71.

It is to be noted that a rearward protruding portion 74a2 having the same structure as the rearward protruding portion 83a2 of the curving piece member 83a is protruded on a rear end side of the distal end section 74. The turning shaft 83b for the up and down directions is inserted into each of portions (two positions) where this rearward protruding portion 74a2 overlaps the frontward protruding portion 83a1 of the curving piece member 83a at a forefront end position of the operation curving section 80, and the rear end side of the distal end section 74 is thereby coupled with the curving piece member 83a at the forefront end position in the operation curving section 80 to allow their turning motion in one direction alone around the turning shaft 83b (around the X axis in FIG. 12 and FIG. 13).

Furthermore, two wire holding members 83d are fixed on an inner peripheral surface of the curving piece member 83a.

These two wire holding members 83*d* are arranged at positions apart from each other by 180° in the circumferential direction of each curving piece member 83*a*, and each of these members is arranged at an intermediate position between the pair of frontward protruding portions 83*a*1 (a position apart from the frontward protruding portion 83*a*1 at 90° in the circumferential direction).

Distal end portions of two operation wires 84 inserted into the respective wire holding members 83*d* are fixed to the distal end section 74.

Moreover, proximal end portions of the two operation wires 84 are coupled with the up-down direction curving operation knob of the dial in the hand operating section. When the curving operation knob is operated, the operation curving section 80 can curve around the turning shafts 83*b* as the X axis in the up and down turning directions at a desired angle. A distal end portion of the second curving section 81 is coupled with a rear end side of the operation curving section 80.

The second curving section 81 is a coupled structure of second curving piece members 85*a* in which the second curving piece members 85*a* are aligned along the center line direction of the flexible curving structure 75. A pair of tongue-shaped frontward protruding portions 85*a*1 protruding frontward are formed at a front end portion of each second curving piece member 85*a*, and a pair of tongue-shaped rearward protruding portions 85*a*2 protruding rearward are formed at a rear end portion of the same. The pair of frontward protruding portions 85*a*1 are arranged at positions apart from each other by 180° in the circumferential direction of each second curving piece member 85*a*. The pair of rearward protruding portions 85*a* are likewise arranged at positions apart from each Other by 180° in the circumferential direction of each second curving piece member 85*a*.

Additionally, in the second curving section 81, the pair of frontward protruding portions 85*a*1 and the pair of rearward protruding portions 85*a*2 of each second curving piece member 85*a* are arranged at positions deviating from positions corresponding to front and back directions (the same positions in the circumferential direction of each second curving piece member 85*a*) by 90°. Further, a turning shaft 85*b*1 such as a hinge pin or a rivet for curving in left and right directions is inserted into each of portions (two positions) where the rearward protruding portion 85*a*2 of the front second curving piece member 85*a* overlaps the frontward protruding portion 85*a*1 of the adjacent rear curving piece member 85*a*, and the front and rear curving piece members 85*a* are coupled with each other to allow their turning motion around each turning shaft 85*b*1 in one direction only (around the Y axis in FIG. 12).

Further, in the second curving section 81, since the pair of frontward protruding sections 85*a*1 and the pair of rearward protruding section 85*a*2 of each second curving piece member 85*a* are arranged at the positions deviating from the positions corresponding to the front and back directions (the same positions in the circumferential direction of each second curving piece member 85*a*) by 90° respectively, turning shafts 85*b*2 for curving in the up and down directions are arranged adjacent to the turning shafts 85*b*1 for the left and right directions respectively. Furthermore, coupling is achieved to allow a turning motion in only one direction around each turning shaft 85*b*2 for the up and down directions (around the X axis in FIG. 12). Thus, in the second curving section 81, the turning shafts 85*b*1 for the left and right directions and the turning shafts 85*b*2 for the up and down directions are alternately arranged along the center line direction of the flexible curving structure 75. Consequently, the curving easy direction is regulated to four directions, i.e., the up and down directions and the left and right directions of the endoscope 71 by the second curving section 81, thereby forming a two-direction curving regulating section whose curving easy direction is regulated to two directions, i.e., the up and down directions (up-down) of the endoscope 71 indicated by the arrow A in FIG. 13, and two directions, i.e., the left and right directions (left-right) indicated by an arrow B in FIG. 13 to the periaxial direction of the center line of the flexible curving structure 75.

It is to be noted that, in the coupling portion of the rear end side of the operation curving section 80 and the distal end portion of the second curving section 81, the turning shaft 85*b*2 for the up and down directions is inserted into each of portions (two positions) where the rearward protruding portion 83*a*2 of the curving piece member 83*a* at the rearmost end position of the operation curving section 80 overlaps the frontward protruding portion 85*a*1 of the second curving piece member 85*a* at the foremost end position of the second curving section 81, and the curving piece member 83*a* at the rearmost end position of the operation curving section 80 is thereby coupled with the second curving piece section 85*a* at the foremost end position of the second curving section 81 to allow their turning motion around each turning shaft 85*b*2 (around the X shaft in FIG. 12) in one direction only.

Since the operation wires 84 are not connected to the second curving piece member 85*a* of the second curving section 81, the second curving piece members 85*a* do not turn even if the operation wires 84 are pulled, but they can curve in desired two directions (directions to rotate around the X axis and the Y axis in FIG. 13) around the turning shafts 85*b*1 for the left and right directions and the turning shafts 85*b*2 for the up and down directions when an external force acts on the distal end insertion tube 72 due to pressing of the distal end insertion tube 72 against an external structure. A distal end portion of the free curving section 79 is coupled with the rear end side of the second curving section 81.

The free curving section 79 is formed of a flexible tube 86 such as a fluorine-containing tube having, e.g., a bucking prevention coil which can curve in free directions wound thereon. Since the operation wires 84 are not connected to the free curving section 79 either, the free curving section 79 cannot be curved by an operation of the curving operation knob of the hand operating section, but can be curved in a shape similar to a shape of, e.g., an external structure having the distal end insertion tube 72 inserted therein.

It is to be noted that a frontward protruding portion 79*a*1 having the same configuration as the frontward protruding portion 85*a*1 of the second curving piece member 85*a* is protruded at the distal end portion of the free curving section 79. The turning shaft 85*b*2 for the up and down directions is inserted into each of portions (two positions) where this frontward protruding portion 79*a*1 overlaps the rearward protruding portion 85*a*2 of the second curving piece member 85*a* at the rearmost end position of the second curving section 81, and the rearward protruding portion 85*a*2 on the rear end side of the second curving piece member 85*a* is coupled with the frontward protruding portion 79*a*1 at the distal end portion of the free curving section 79 to allow their turning motion around each turning shaft 85*b*2 in one direction only (around the X axis in FIG. 12 and FIG. 13).

Moreover, the shape sensor 73 according to this embodiment is arranged to be parallel to an outer peripheral surface of a treatment tool insertion channel 82 arranged in the distal end insertion tube 72 of the endoscope 71 and, in this state, is fixed and held on at least a part thereof by using an adhesive or the like. In the shape sensor 73, a first shape sensor constituent section 91 arranged at a position corresponding to the operation curving section 80, a second shape sensor constituent section 92 arranged at a position corresponding to the second curving section 81, and a third shape sensor constituent section 93 arranged at a position corresponding to the free curving section 79 are provided. The first shape sensor constituent section 91 has at least one detection object section 94a disposed in the range of the operation curving section 80. Additionally, the second shape sensor constituent section 92 has at least two detection object sections 94b disposed in the range of the second curving section 81, and the third shape sensor constituent section 93 has at least two detection object sections 94c disposed in the range of the free curving section 79.

Further, the first shape sensor constituent section 91 has, e.g., the curving direction regulating section 3 of the shape sensor 1 according to the first embodiment (see FIG. 1 and FIG. 2) or the curving direction regulating section 45 of the shape sensor 41 according to the fourth embodiment (see FIG. 6 and FIG. 7) incorporated therein. Consequently, in the range corresponding to the operation curving section 80, coupling is achieved by sensor pieces 96 that can curve in a direction to rotate around the X axis by a shaft 95 parallel to the turning shafts 83b. The second shape sensor constituent section 92 has, e.g., the core member 21 of the shape sensor 1 according to the second embodiment (see FIG. 5A) or the core member 31 of the shape sensor 1 according to the third embodiment (see FIG. 5B) incorporated therein. Consequently, in the range corresponding to the second curving section 81, coupling is achieved by the sensor pieces 96 that can curve in a direction to rotate around the X axis or the Y axis by an axis parallel to the turning shafts 85b2 and an axis parallel to the turning shafts 85b1. Moreover, the third shape sensor constituent section 93 has no mechanism to regulate a curving direction provided in the range corresponding to the free curving section 79 in particular, and can curve in free directions.

A function and an effect of this embodiment will now be described.

In the shape sensor 73, for example, the curving piece members 83a curve in the up and down turning directions alone around the turning shafts 83b corresponding to the X axis by operating the operation wires 84 in the operation curving section 80. At this time, the channel 82 also curves in tandem with the curving piece members 83a, and the first shape sensor constituent section 91 of the shape sensor 73 disposed in the channel 82 likewise curves. At this time, since the sensor pieces 96 in the first shape sensor constituent section 91 curve in a curvable direction A to rotate around the X axis by the shaft 95, the curving direction of the distal end insertion tube 72 of the endoscope 71 substantially coincides with the curving direction of the first shape sensor constituent section 91.

Additionally, in the second curving section 81, curving is likewise possible in the direction to rotate around the X axis or the Y axis, and the curving direction of the distal end insertion tube 72 of the endoscope 71 substantially coincides with the curving direction of the second shape sensor constituent section 92 of the shape sensor 73. In the free curving section 79, both the distal end insertion tube 72 of the endoscope 71 and the third shape sensor constituent section 93 of the shape sensor 73 can curve in free directions.

As described above, in the shape sensor 73 according to this embodiment, since both the first shape sensor constituent section 91 and the second shape sensor constituent section 92 of the shape sensor 73 are arranged so that they can curve in a direction along which the distal end insertion tube 72 of the endoscope 71 can curve in the range where the curvable direction of the distal end insertion tube 72 of the endoscope 71 is regulated, it is possible to provide the tubular insertion system in which the shape sensor 73 can be hardly distorted even though the distal end insertion tube 72 of the endoscope 71 curves. Thus, it is possible to provide the tubular insertion system that can highly possibly detect a shape of the distal end insertion tube 72 of the endoscope 71 with a high accuracy.

Further, in this embodiment, the shape sensor 73 is disposed on the channel 82, but it may be disposed on any other curvable built-in element arranged in the flexible curving structure 75, e.g., an air supply/water supply A/W tube 101 connected to a non-illustrated air supply/water supply nozzle of the distal end section 74 or a jet water supply J tube 102 connected to a non-illustrated jet water supply opening portion of the distal end section 74 as shown in FIG. 13.

The invention claimed is:

1. A shape sensor comprising:
a light source;
a shape sensor main body which comprises at least one optical fiber and an optical characteristic material, wherein
the optical fiber comprises a core extending within the optical fiber and a cladding around the core, the optical fiber configured to receive, at one end of the shape sensor main body, detection light emitted from the light source and to propagate the detection light by the core and the cladding,
the optical characteristic material disposed in an opening at a portion of an outer periphery of the optical fiber, the opening extending up to the core, the optical characteristic material being configured to one of absorb or wavelength-convert the detection light, and
the shape sensor main body is configured to allow for measurement of a shape of the optical fiber based on a change in characteristics of the detection light, the characteristics of the detection light being changed by the optical characteristic material in accordance with a change in curvature of the optical fiber;
an optical sensor disposed at the one end of the shape sensor main body and configured to receive, from the optical fiber, the detection light having passed through the optical characteristic material, and to photoelectrically convert the received detection light into an electric signal indicative of a light quantity; and
a curving direction regulator comprising an elastic core member comprising a rectangular cross section and fixed onto the outer periphery of the optical fiber by a bonding member along a light propagating direction of the optical fiber, the curving direction regulator configured to regulate, by an elastic force of the core member, the optical fiber from curving in a direction of a short side of the rectangular cross section of the core member.

2. The shape sensor according to claim 1, wherein the core member of the curving direction regulator comprises four rectangular cross sections as ribs that together form two planes orthogonal to each other at 90° to form an X-shaped profile, wherein a bending rigidity of the core member in planar directions of the respective two planes is stronger than a bending rigidity of the core member in a direction dividing, into two equal portions, an angle between the two planes.

3. The shape sensor according to claim 1,
wherein the core member comprises core materials aligned therein, and
a bending rigidity of the core member is weak in a direction along which the core materials are aligned is weaker than a bending rigidity of the core member in a direction orthogonal to the direction along which the core materials are aligned.

4. The shape sensor according to claim 3,
wherein the shape sensor main body comprises annular fiber holders each comprising one or more openings to hold the at least one optical fiber, respectively, the fiber holders arranged along the light propagating direction with intervals, and
the bending rigidity of the core member is regulated by an arrangement of the core materials varying in bending rigidities in the fiber holders.

5. The shape sensor according to claim 4, wherein the curving direction regulator is arranged near a center of each of the fiber holders, and the optical fiber is arranged on an outer peripheral side of the curving direction regulator.

6. The shape sensor according to claim 4, wherein the curving direction regulator is arranged on or near an outer periphery of each of the fiber holders, and the optical fiber is arranged inside a maximum circumscribed circle defined by an outermost peripheral portion of the curving direction regulator.

7. The shape sensor according to claim 4, wherein a curvable direction of the shape sensor and a direction for detecting curving of the optical fiber are coincide with each other at least in a range where the curving is regulated, and the optical fiber and each of the fiber holders are bonded.

8. A tubular insertion system comprising:
an insertion tube that is inserted into a tube space and has a curving section that curves; and
the shape sensor according to claim 1 that detects a curved shape of at least a part of the insertion tube,
wherein the shape sensor is mounted or incorporated in the insertion tube such that the curving direction regulator of the shape sensor regulates the optical fiber from curving in a direction different from a direction in which the curving section of the insertion tube curves.

9. A tubular insertion system comprising:
an insertion tube that is inserted into a tube space and has a curving section that curves; and
the shape sensor according to claim 1 that detects a curved shape of at least a part of the insertion tube,
wherein the shape sensor is mounted or incorporated in the insertion tube such that a strength required to curve the insertion tube is larger than a strength required to curve the shape sensor in a direction in which the curving section of the insertion tube curves.

10. A shape sensor comprising:
a light source;
a shape sensor main body which comprises a plurality of optical fibers and a plurality of optical characteristic materials corresponding to the respective optical fibers, wherein
the optical fibers are different in bending rigidities and each comprise a core extending within the optical fiber and a cladding around the core, the optical fibers each configured to receive, at one end of the shape sensor main body, detection light emitted from the light source and to propagate the detection light by the core and the cladding,
the optical characteristic materials are each disposed in an opening at a portion of an outer periphery of the corresponding optical fiber, the opening extending up to the core, the optical characteristic materials each configured to absorb or wavelength-convert the detection light, and
the shape sensor main body is configured to allow for measurement of a shape of the optical fibers based on a change in characteristics of the detection light, the characteristics of the detecting light being changed by the optical characteristic materials in accordance with a change in curvature of the optical fibers;
an optical sensor disposed at the one end of the shape sensor main body and configured to receive, from the optical fibers, the detection light having passed through the respective optical characteristic materials, and to photoelectrically convert the received detection light into an electric signal indicative of a light quantity; and
a pair of core members disposed between the optical fibers of different bending rigidities, the pair of core members configured to regulate the optical fibers from curving in a direction where the bending rigidities of the optical fibers are small.

11. The shape sensor according to claim 10, wherein the optical fibers of different bending rigidities differ in materials of one of the cores or the coating.

* * * * *